United States Patent [19]
Mancy et al.

[11] 3,997,661
[45] Dec. 14, 1976

[54] PROCESS FOR THE PREPARATION OF DAUNORUBICIN BY CULTIVATING A STREPTOMYCES SPECIES

[75] Inventors: Denise Mancy, Charenton; Leon Ninet; Jean Preud'Homme, both of Paris, all of France

[73] Assignee: Rhone-Poulenc S.A., Paris, France

[22] Filed: Nov. 14, 1968

[21] Appl. No.: 775,904

[30] Foreign Application Priority Data

Nov. 15, 1967 France .............................. 67.128323

[52] U.S. Cl. .............................. 424/118; 424/120; 424/181
[51] Int. Cl. .......................................... A61k 21/00
[58] Field of Search .......................... 424/115–123, 424/181

[56] References Cited
FOREIGN PATENTS OR APPLICATIONS
985,598   3/1965   United Kingdom ............... 424/118

*Primary Examiner*—Albert T. Meyers
*Assistant Examiner*—Daren M. Stephens
*Attorney, Agent, or Firm*—Stevens, Davis, Miller & Mosher

[57] ABSTRACT

The antibiotic daunorubicin is prepared by aerobically cultivating the microorganism *Streptomyces griseus*, var. *rubidofaciens*, DS 32,041 (NRRL 3383), or a daunorubicin-producing mutant thereof, using an aqueous nutrient medium containing assimilable sources of carbon, nitrogen and inorganic substances, and separating daunorubicin formed during the culture.

12 Claims, No Drawings

PROCESS FOR THE PREPARATION OF DAUNORUBICIN BY CULTIVATING A STREPTOMYCES SPECIES

This invention relates to a new process for the preparation of the antibiotic designated 13057 R.P., which has received the name "daunorubicin" (previously known as "rubidomycin").

In British Patent No. 985,598 entitled "Improvements in or relating to Antibiotics and their preparation" granted to Rhone-Poulenc S.A. on an application filed May 16, 1963, there have been described the antibiotic designated 9865 R.P., its three constituents designated 13213 R.P., 13057 R.P. (or daunorubicin) and 13330 R.P., the aglycone of 9865 R.P. designated 13567 R.P., the preparation of the antibiotic 9865 R.P. by cultivation of Streptomyces 8899 or Streptomyces 31723 in an appropriate nutrient medium, and the separation of the antibiotic 9865 R.P. into its constituents.

As stated in the said Patent, daunorubicin is a base which forms acid solution salts. The free base is an amorphous red powder soluble in alcohols and chloroform, very slightly soluble in water and ketones and practically insoluble in benzene and diethyl ether; it contains carbon, hydrogen, oxygen and nitrogen in the following proportions, $C = 59.8\%$, $H = 5.85\%$, $N = 2.3\%$, $O = 29.45\%$; it melts at 155°–170° C. (with decomposition); its ultra-violet spectrum (as determined on a solution in 96% ethanol) shows absorption maxima at 236 m$\mu$, $E_{1\ cm.}^{1\%} = 621$, 255 m$\mu$, $E_{1\ cm.}^{1\%} = 426$, 290–295 m$\mu$, $E_{1\ cm.}^{1\%} = 135$, and 482–498 m$\mu$, $E_{1\ cm.}^{1\%} = 230$, and absorption minima at 245 m$\mu$, $E_{1\ cm.}^{1\%} = 378$, 280 m$\mu$, $E_{1\ cm.}^{1\%} = 122$, and 325 m$\mu$, $E_{1\ cm.}^{1\%} = 10$, and a shoulder at 533 m$\mu$, $E_{1\ cm.}^{1\%} = 127$; its infrared spectrum (as determined on tablets in mixture with potassium bromide) shows the following principal absorption bands:

| | | | | | | | | |
|---|---|---|---|---|---|---|---|---|
| about | 3450 | vS | 1410 | S | | 1205 | S | 1068 m |
| | 2925 | S | 1380 | S | about | 1190 | sh | 1033 m |
| | 1715 | m | 1355 | S | | 1150 | sh | 1010 S |
| | 1615 | S | 1282 | S | | 1117 | S | 983 S |
| | 1582 | S | 1262 | Sh | | 1090 | m | 950 w |
| | 1447 | S | 1230 | S | | 1080 | m | 918 w |
| | 867 | w | 815 | m | | 790 | m | 762 m |
| about | 840 | w | | | | | | |

```
vS = very strong
 S = strong
 m = medium
 w = weak
sh = shoulder
```

The present invention is concerned with a new process for the preparation of daunorubicin by cultivation, under aerobic conditions, of a new microorganism more completely identified hereinafter which belongs to the genus Streptomyces, designated by the name *Streptomyces griseus*, var. *rubidofaciens*, strain D.S. 32,041, and which has been isolated from a soil sample taken in Bengal, India.

A specimen of this new microorganism has been deposited with the United States Department of Agriculture, Northern Regional Research Laboratory, at Peoria, Ill., United States of America, under the number NRRL 3383. Specimens of the new microorganism may be obtained from this Laboratory on reference to the present patent application.

The new strain of Streptomyces has essential characteristics from which it may be concluded that it belongs to the series *Streptomyces griseus* of S. A. Waksman ("The Actinomycetes", Vol. II, S. A. Waksman, The Williams and Wilkins Company, Baltimore, 1961, pages 133–143). Very close in its characteristics to the species representative of this series, *Streptomyces griseus* Waksman and Henrici, which produces streptomycin, and which constitutes the species described in "Bergey's Manual of Determinative Bacteriology" (7th edition, The Williams and Wilkins Company, Baltimore, 1961, page 791), it differs essentially therefrom in that it does not produce any streptomycin, but on the other hand a very characteristic, and often abundant, deep red soluble pigment which is generally related with an antibiotic activity. However, it is so close to this species in all its other characteristics that it can be regarded as a variety thereof, and it has been named *Streptomyces griseus*, var. *rubidofaciens*, strain DS 32,041.

*S. griseus*. var. *rubidofaciens*, strain DS 32,041 does not produce any melanic pigment on organic media. It forms straight or slightly flexuous sporophores, separately inserted or having a few bunched branches. Its spores are oval to cylindrical and have rounded ends, measuring 0.4 to 0.7 $\mu$/0.8 to 1.2 $\mu$. Its sporulated aerial mycelium, which is abundant and of powdery aspect and a light greenish yellow-grey colour, has the characteristic appearance of that of a strain of *Streptomyces griseus;* often, some zones of this aerial mycelium take on a pink shade when the red soluble pigment is produced and colours the subjacent culture medium.

In the following Table, there are given the cultural characteristics and biochemical properties presented by *S. griseus*, var. *rubidofaciens*, strain DS 32,041, on a number of nutrient agars and nutrient broths usually employed to examine the appearance of strains of Streptomyces. Unless otherwise stated, these characteristics and properties are those exhibited by cultures aged about 2 weeks at 25° C., which have reached a good stage of development. A number of the culture media employed were prepared from the formulae indicated in "The Actinomycetes" (S. A. Waksman, Chronica Botanica Company, Waltham, Mass., U.S.A., 1950, pp. 193–197); in this case, they are indicated by the letter W, followed by the number allocated to them in "The Actinomycetes".

The references or compositions of the other media are the following:

Ref. A - K. L. Jones - Journal of Bacteriology 57, 142 (1949)

Ref. B - Formula W-23 with the addition of 2% of agar

Ref. C - "Hickey and Tresner's Agar" - T. G. Pridham et al - Antibiotics Annual, 1956–1957, p.950

Ref. D - "Yeast Extract Agar" - T. G. Pridham et al - Antibiotics Annual, 1956–1957, p.950

Ref. E - "Tomato Paste Oatmeal Agar" - T. G. Pridham et al - Antibiotics Annual, 1957–1957, p.950

Ref. E - W. E. Grundy et al - Antibiotics and Chem. 2, 402 (1952)

Ref. G - "Inorganic Salts — Starch Agar" - T. G. Pridham et al - Antibiotics Annual, 1956–1957, p.951

Ref. H - corresponds to the formula W-1, in which 30 g. of sucrose are replaced by 15 g. of glucose Ref. I - corresponds to the formula W-1, in which 30 g. of sucrose are replaced by 15 g. of glycerine Ref. J - "Plain gelatin" - prepared in accordance with the instructions in "Manual of Methods for Pure Culture Study of Bacteria", Society of American Bacteriologists, Geneva, N.Y. II$_{50}$ – 18 (May 1950)

Ref. K - "Manual of Methods for Pure Culture Study of Bacteria" Society of American Bacteriologists, Geneva, N.Y. II$_{50}$ - 19 (May 1950)

Ref. L - "Manual of Methods for Pure Culture Study of Bacteria" Society of American Bacteriologists, Geneva, N.Y. II$_{50}$ - 18 (May 1950)

Ref. M - corresponds to the formula W-18, in which sucrose is replaced by small strips of filter paper partially immersed in the liquid Ref. N - Skimmed milk as a commercially available powder, reconstituted in accordance with the manufacturers instructions Ref. P - The Actinomycetes, Vol. 2, p.333 - No. 42 - S. A. Waksman, The Williams and Wilkins Company, Baltimore (1961).

Ref. Q - H. D. Tresner and F. Danga - Journal of Bacteriology, 76, 239–244 (1958).

| Culture medium | Degree of development | Vegetative mycelium (V.m.) or underside of the culture | Aerial structure (comprising the combination of the aerial mycelium and of the sporulation) | Soluble pigment | Observations and biochemical properties |
|---|---|---|---|---|---|
| Bennett's agar (Ref.A) | Good | V.m. red Underside red | Light greenish yellow-grey to greyish pink. Moderately developed. | Slightly orange red | |
| Emerson's agar (Ref.B) | Good | V.m. red Underside red | Light greenish yellow-grey to pale pink. Moderately developed. | Slightly brownish orange-red | |
| Hickey and Tresner's agar (Ref.C) | Good | Underside orange-brown | Light greenish yellow-grey to greyish pink. Moderately developed. | Slightly reddish orange-brown | Oval to cylindrical spores having rounded ends, measuring 0.4 to 0.7 $\mu$/0.8 to 1.2 $\mu$. Straight or slightly flexuous sporophores, isolated or bunched. |
| Pridham's yeast extract agar (Ref.D) | Good | V.m. red Underside brownish-red | Light greenish yellow-grey to greyish pink. Moderately developed. | Deep red | |
| Pridham's tomato paste oatmeal agar (Ref.E) | Good | Underside light brownish-red | Light greenish yellow-grey to greyish pink. Very well developed. | Light reddish-brown | |
| Glucose-peptone agar (W-6) | Fairly good | Underside reddish orange | Light greenish yellow-grey. Moderately developed. | Slightly brownish reddish orange | |
| Nutrient agar (W-5) | Medium | Underside reddish orange | Whitish to light pink-yellow. Moderately developed. | Light reddish orange | |
| Krainsky's calcium malate agar (Ref.F) | Moderate | Underside light pink-brown | Light greenish yellow-grey with some light greyish pink spots. Very moderately developed. | Light brownish pink | Solubilisation of calcium malate: positive |
| Glucose-asparagine agar (W-2) | Fairly good | Underside light red to light orange | Light greenish yellow-grey to pink. Moderately developed. | Light reddish orange | |
| Glycerine-asparagine agar (W-3) | Good | Underside light orange-red | Light greenish yellow-grey to pink. Fairly well developed. | Light orange-reddish-brown | |
| Pridham's starch agar (Ref.G) | Good | Underside reddish orange | Light greenish yellow-grey to greyish pink. Well developed. | Light reddish brown | Hydrolysis of starch: positive. Oval to cylindrical spores having rounded ends, measuring 0.4 to 0.7 $\mu$/0.8 to 1.2$\mu$. Straight or slightly flexuous sporophores, isolated or bunched. |
| Czapek's synthetic glucose agar (Ref.H) | Good | Underside slightly violet light brownish-red. | Light greenish yellow-grey to pale pink. Well developed. | Light violet-red | |
| Czapek's synthetic glycerine agar (Ref.I) | Good | Underside light brownish-red | Light greenish yellow-grey to light pink. Well developed. | Pink | |
| Potato culture (W-27) | Very Good | V.m. thick and wrinkled. Red | Light greenish yellow-grey to pink. Medium development. | Weak brownish-red | |
| 12% pure gelatin (Ref.J) | Medium | Whitish to brownish yellow and pink-brown colonies, on the surface of the gelatin | Whitish, traces | Belated. Almost nil at the end of 2 weeks. Brownish-yellow, in very small quantity close to the surface, after culture for 3 or 4 weeks | Liquefaction of the gelatin fairly good. |
| Dimmick's glucose-nitrate broth (Ref.K) | Medium | Light skin Underside pink | Whitish to light pink. Very moderately developed. | Light pink | Nitrite reaction: positive |
| Nitrated nutrient broth (Ref.L) | Fairly good | Ring made up of colonies having a pink underside | Whitish. Poorly developed. | Nil | Nitrite reaction: positive |
| Czapek's cellulose broth (Ref.M) | Good | V.m. light pink, in skin on the surface of the broth | Very light greyish yellow. Moderately developed on the paper sticking out from the broth | Very light pink | Utilisation of cellulose: positive. Nitrite reaction: positive |
| Skimmed milk (Ref.N) | Good | Light brownish to red ring | Nil | | Peptonisation slow, beginning at the end of 2 weeks, almost |

-continued

| Culture medium | Degree of development | Vegetative mycelium (V.m.) or underside of the culture | Aerial structure (comprising the combination of the aerial mycelium and of the sporulation) | Soluble pigment | Observations and biochemical properties |
|---|---|---|---|---|---|
| Tyrosine-yeast extract agar for the formation of melanin (Ref.P) | Medium | Underside light, slightly orange brown-yellow | Very light yellow-grey Medium development. | Weak, slightly pink brownish | complete in one month. No coagulation. pH changing from 6.3 to 7.5 in one month Formation of melanin: negative |
| Tresner and Danga's agar (Ref.Q) | Good | | | | Production of H₂S: negative |

The capacity of S. griseus, var. rubidofaciens, strain DS 32,041 to utilize various sources of carbon and nitrogen to ensure its development has been determined in accordance with the principle of the method of Pridham and Gottlieb [J. of Bact. 56, 107–114 (1948)]. The degree of development was observed on the basic medium indicated by the authors, either replacing glucose by the various sources of carbon respectively tested, or replacing $(NH_4)_2SO_4$ by the various sources of nitrogen respectively tested. The results are indicated in the following Table:

| Carbon sources tested | Utilisation | Nitrogen sources tested | Utilisation |
|---|---|---|---|
| D-Ribose | positive | NaNO₃ | positive |
| D-Xylose | positive | NaNo₂ | positive |
| L-Arabinose | negative | (NH₄)₂SO₄ | positive |
| L-Rhamnose | negative | (NH₄)₂HPO₄ | positive |
| D-Glucose | positive | Adenine | positive |
| D-Galactose | positive | Adenosine | positive |
| D-Fructose | positive | Uracil | negative |
| D-Mannose | positive | Urea | positive |
| L-Sorbose | negative | L-Asparagine | positive |
| Lactose | Slow and moderate | Glycine | positive |
| Maltose | positive | Sarcosine | negative |
| Sucrose | negative | DL-Alanine | positive |
| Trehalose | negative | DL-Valine | positive |
| Cellobiose | positive | DL-Aspartic acid | positive |
| Raffinose | negative | L-Glutamic acid | positive |
| Dextrin | positive | L-Arginine | positive |
| Inulin | negative | L-Lysine | positive |
| Starch | positive | DL-Serine | positive |
| Glycogen | positive | DL-Threonine | positive |
| Glycerin | positive | DL-Methionine | negative |
| Erythritol | negative | Taurine | negative |
| Adonitol | negative | DL-Phenylalanine | positive |
| Dulcitol | negative | L-Tyrosine | positive |
| D-Mannitol | positive | DL-Proline | positive |
| D-Sorbitol | negative | L-Hydroxyproline | positive |
| Inositol | negative | L-Histidine | positive |
| | | Betaine | negative |

S. Griseus, var. rubidofaciens, strain DS 32,041 differs from the species distinguished by S. A. Waksman within the series of the strains of S. Griseus, of which none of those hitherto described gives a soluble red pigment comparable to that produced by the strain DS 32,041 nor gives any production of an antibiotic and anti-tumour substances effective in treating certain tumors, namely lymphosarcoma, nephroblastoma, neuroblastoma, acute lymphoblastic leukemia, and acute myeloblastic leukemia, identical to daunorubicin (The Actinomycetes, Vol. II, S. A. Waksman, The Williams and Wilkins Company, Baltimore, 1961, pages 140–143).

It has already been stated that S. griseus, var. rubidofaciens, strain DS 32,041, which produces a soluble red pigment, is different from S. griseus Waksman and Henrici — it is also not identical to S. griseinus Waksman which produces grisein — neither of these known microorganisms producing characteristic soluble pigments in their cultures, except for certain strains of S. griseus which produce streptomycin and form a green soluble pigment on calcium malate medium, which property is not possessed by S. griseus, var. rubidofaciens, strain DS 32,041. Likewise, this strain is different from Streptomyces coelicolor (Muller), which produces candicidin, and gives a soluble blue pigment, and Streptomyces californicus Waksman and Curtis, which produces viromycin, and which has on certain media a pink to purple pigmentation of the mycelium, due to an endocellular pigment which does not diffuse into the culture medium, but does not produce any soluble red pigment. Finally, it is also different from Streptomyces chrysomallus (Lindenbein) Waksman, which produces actinomycin and which gives a soluble gold-yellow pigment but never a soluble red pigment.

In accordance with the conceptions of S. A. Waksman, the strain DS 32,041 should perhaps also be considered as a new species.

The essential differences between the strain DS 32,041 and the species S. griseus lie only in the production of soluble antibiotic pigment, and the strain Streptomyces griseus, var. rubidofaciens, DS 32,041 may therefore be regarded as a variety of the species S.

*griseus* already described by S. A. Waksman and not as a different species.

The process for the preparation of daunorubicin according to the present invention comprises aerobically cultivating *Streptomyces griseus, var. rubidofaciens*, DS 32,041, or a daunorubicin-producing mutant thereof, using an aqueous nutrient medium containing assimilable sources of carbon, nitrogen and inorganic substances, and separating the antibiotic daunorubicin formed during the culture.

The cultivation of *Streptomyces griseus, var. rubidofaciens*, DS 32,041 by fermentation essentially produces daunorubicin, but the other constituents 13213 R.P. and 13330 R.P. of the antibiotic 9856 R.P. are also produced. They are separated from daunorubicin during the course of the extraction and purification operations and may optionally be isolated, but the main object of the present invention is the preparation of daunorubicin.

The culture of *Streptomyces griseus, var. rubidofaciens*, DS 32,041 may be carried out by any of the known aerobic surface or submerged culture methods, the latter being preferred because they are more convenient. Conventional types of apparatus currently used in the fermentation industry may be employed.

In particular, the following sequence of operations may be adopted:

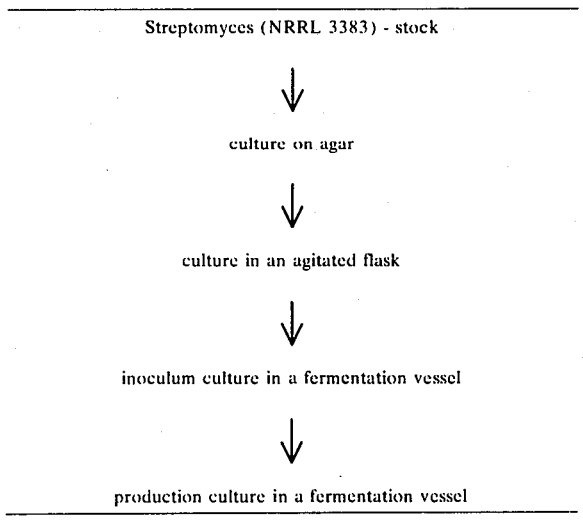

The fermentation medium must contain assimilable sources of carbon, nitrogen and inorganic substances, and optionally growth-promoting factors; all these ingredients may be supplied as well-defined products or complex mixtures, such as are found in natural biological products of various origins.

As the assimilable source of carbon there may be used carbohydrates such as glucose, maltose, dextrins, starch or other carbon-, hydrogen- and oxygen-containing substances such as the sugar alcohols, e.g. mannitol, or certain organic acids, e.g. lactic or citric acid. Certain animal or vegetable oils such as lard oil or soyabean oil may be advantageously used instead of, or in admixture with, carbon-, hydrogen- and oxygen-containing substances.

A very wide range of suitable sources of assimilable nitrogen is available. The sources may be very simple chemical compounds such as nitrates, inorganic and organic ammonium salts, urea, or amino-acids. It may also be complex substances containing principally nitrogen in protein form, e.g. casein, lactalbumin, gluten and their hydrolysates, soyabean flour, peanut meal, fish meal, meat extract, yeast extract, distillers' solubles and corn steep liquor.

Of the inorganic substances added, some may have a buffering or neutralizing effect, such as the alkali metal phosphates or alkaline earth metal phosphates, or the carbonates of calcium and magnesium. Others contribute to the ionic equilibrium needed for the development of *Streptomyces griseus, var. rubidofaciens*, DS 32,041 and for the production of the antibiotic, examples of these are the chlorides and sulphates of the alkali metals and alkaline earth metals. Finally, some of them act more especially as activators of the metabolism of Streptomyces DS 32,041: to these belong the salts of zinc, cobalt, iron, copper and manganese.

The pH value of the fermentation medium at the beginning of the culture should be within the range 6.0 to 7.8, and preferably from 6.5 to 7.5. The optimum fermentation temperature is 25°–30° C., but satisfactory production is achieved at temperatures of from 23° to 33° C. The rate of aeration of the fermentation vessels may vary between quite wide limits, but it has been found that an aeration rate of 0.3 to 3 liters of air per liter of broth per minute is particularly suitable. The maximum yield of antibiotic is obtained after 2 to 8 days of growth, but the period depends predominantly on the medium used.

From the foregoing it will be realised that the general conditions for the culture of *Streptomyces griseus, var. rubidofaciens*, DS 32,041 for the production of daunorubicin may be widely varied and adapted as appropriate to the circumstances.

Daunorubicin may be isolated from the fermentation broths by various methods. The culture broth can be filtered at a pH between 1.5 and 9 and, under these conditions, the major part of the active material passes into the filtrate. After washing with water, the filter cake retains practically no active material. It is advantageous to carry out this operation in acid medium, and particularly one acidified with oxalic acid to a pH between 1.5 and 2. It is also possible to carry out the filtration at a pH between 2 and 7, preferably near to 2, in the presence of an aliphatic alcohol containing from 1 to 3 carbon atoms.

In these extraction operations, daunorubicin is obtained in aqueous or aqueous-alcoholic solution, and it is then brought into organic solution by extraction with a water-immiscible organic solvent such as butanol, methyl isobutyl ketone, ethyl acetate or chloroform, at a pH between 5.5 and 9, preferably about 7.5. This extraction is optionally preceded by a treatment on an ion-exchange resin, in which case the aqueous solution is adjusted to a pH of about 4 and then treated with a cation exchange resin. Daunorubicin is eluted, preferably with methanol containing 10% of water and 1% of sodum chloride. The eluate is then concentrated to remove the alcohol and extracted as described above.

The fermentation broth may also be directly extracted with a water-immiscible organic solvent such as butanol, ethyl acetate or chloroform, at a pH betwen 5.5 and 9, preferably about 7.5. In this case, all the active material passes into the organic phase, which is separated from the aqueous phase by the usual methods.

Whatever the method of extraction chosen, daunorubicin is finally obtained in organic solution. It may be advantageous at this stage to purify the antibiotic by successively bringing it into aqueous solution and then into organic solution by varying the pH. The crude antibiotic may be isolated from the organic solution last obtained by concentration or precipitation with a poor solvent for the antibiotic such as hexane. A particularly advantageous method of isolation consists of acidifying the organic solution to a pH of about 4, preferably with acetic acid, and concentrating it under reduced pressure to a small volume. The addition of a poor solvent for daunorubicin, for example hexane, to the concentrate obtained causes precipitation of the crude antibiotic.

To obtain daunorubicin in a purer state, all the usual methods may be employed, such as chromatography on various adsorbent substances, counter-current distribution or partition between various solvents.

Daunorubicin may also be converted to acid addition salts by treatment with acids, for example hydrochloric acid. Such salts may be purified by application of conventional methods.

Daunorubicin obtained by this new method and its acid addition salts exhibit characteristics identical to those of the antibiotic 13057 R.P. and of its acid addition salts described in British Pat. No. 985,598.

The following Examples illustrate the invention.

EXAMPLE 1

A 170-liter fermentation vessel is charged with:
soyabean meal — 3.600 kg.
distillers' solubles — 0.600 kg.
starch — 4.200 kg.
soyabean oil — 1.800 liters
sodium chloride — 1.200 kg.
tap water, to make up to 110 liters.

After the pH of the mixture has been adjusted to 8.45 with concentrated 10N sodium hydroxide solution (120 cc.), the medium is sterilised at 122° C. by bubbling steam through it for 40 minutes. After cooling, the volume of the broth is 120 liters and the pH is 6.80. The broth is then inoculated with 200 cc. of a culture in an agitated Erlenmeyer flask of the strain *Streptomyces griseus, var. rubidofaciens*, DS 32,041. The culture is developed at 30° C. for 35 hours with agitation and aeration with sterile air; it is then ready for inoculation of the production culture.

The production culture is carried out in an 800-liter fermentation vessel charged with the following substances:
soyabean meal — 12 kg.
distillers' solubles — 2 kg.
starch — 2 kg.
soyabean oil — 12 liters
sodium chloride — 4 kg.
tap water, to make up to 370 liters.

After adjustment of the pH of the mixture to 7.50 with concentrated 10N sodium hydroxide solution (250 cc.), the medium is sterilised at 122° C. by bubbling steam through it for 40 minutes. After cooling, the volume of the broth is 400 liters and the pH is 6.80. The broth is then inoculated with 40 liters of the inoculum culture from the 170-liter fermentation vessel. The production culture is carried out at 30° C. for 161 hours with agitation, using a motor revolving at 255 r.p.m., and aeration with 25 m³/hr. of sterile air. The pH of the medium is then 7.0 and the volume of the broth is 350 liters. The quantity of daunorubicin present in the medium is 34 $\mu$g/cc.

EXAMPLE 2

100 liters of culture broth obtained from the fermentation described in Example 1 are placed in a vat provided with a stirrer and a steam heating coil. Oxalic acid (3 kg.) is added and the mass is heated to 50° C. The stirring and the said temperature are maintained for 1 hour, after which time a filtration adjuvant (4 kg.) is added and then the suspension is filtered on a filter-press. The filter cake is washed on the filter with water (110 liters). The filtrate, the volume of which is 190 liters, is cooled to +5° C. and the pH is adjusted to 4.5 by addition of 10% sodium hydroxide solution.

The filtrate is passed through a column containing Amberlite IRC$_{50}$ (4 liters) in acid form, so as to pass through the resin bed from the top downwards at a rate of 15 liters/hr. The column is then washed with water (15 liters) circulating in the same direction as the filtrate and at the same rate, and then with methanol containing 50% of water (25 liters) at a rate of 15 liters/hr. circulating from the bottom upwards, and then with methanol containing 10% of water (50 liters) again at the same rate and from the bottom upwards.

The effluent and the washings are discarded and the column is eluted with a solution circulating from the top downwards through the resin and having the following composition:
sodium chloride — 10 g.
water — 100 cc.
methanol to make up to — 1,000 cc.

The eluate is collected as soon as an orange-red coloration occurs and until this colour disappears. A volume of 50 liters is collected which contains the major part of the antibiotic. The eluate is concentrated under reduced pressure (2 mm.Hg) at 35° C. to a volume of 10 liters.

The concentrate is extracted at pH 7.5 with chloroform (3 × 5 liters). The chloroformic extract is concentrated at 30° C. under reduced pressure (2 mm.Hg) to a volume of 100 cc. The antibiotic is precipitated in the form of the base with 1 liter of hexane, filtered off, washed and dried to give finally 5.5 g. of crude base containing 71% of daunorubicin.

EXAMPLE 3

The product (4.3 g.) obtained in Example 2 is dissolved in a mixture of n-butanol, water and 10N hydrochloric acid (94-5-1 by volume; 43 cc.) to give a daunorubicin hydrochloride solution. Daunorubicin hydrochloride is precipitated by the addition of a mixture of acetone and hexane (50—50 by volume; 430 cc.) The precipitate is filtered off, washed with hexane (43 cc.) and dried at 50° C. under reduced pressure (5 mm.Hg) for 15 hours to give 3 g. of semi-purified daunorubicin hydrochloride (titrating 67% of daunorubicin) in a yield of 66%.

EXAMPLE 4

The semi-purified hydrochloride obtained in Example 3 (2.9 g.) is dissolved in a mixture of n-butanol and water (95-5 by volume; 30 cc.). Acetone (30 cc.) is then gradually added to cause crystallisation of the daunorubidin hydrochloride. The crystals are filtered off, washed with acetone (6 cc.) and dried at 50° C. under reduced pressure (5 mm.Hg) for 15 hours. There are thus obtained 2 g. of hydrochloride (titrating 90% of daunorubicin) in a yield of 92%.

EXAMPLE 5

The crystalline hydrochloride obtained in Example 4 (1.9 g.) is dissolved in a mixture of dioxane and water (80–20 by volume; 24 cc.) and anhydrous dioxan (174 cc.) is slowly run in with reduced stirring to cause crystallisation of the daunorubicin hydrochloride. The crystals are filtered off, washed with anhydrous dioxan (7 cc.) and dried for 15 hours at 50° C. under reduced pressure (5 mm.Hg) to give 1.36 g. of pure daunorubicin hydrochloride in a yield of 75%.

The daunorubicin hydrochloride obtained is soluble in water and alcohols, sparingly soluble in chloroform and insoluble in benzene and diethyl ether.

Daunorubicin hydrochloride has the following elementary composition:

$C = 54.5\%$  $H = 5.55\%$  $N = 2.45\%$  $Cl = 6.1\%$

Its physical properties are:
Appearance — orange red needles
Melting point — 225°–230° C.
Optical rotation — $[\alpha]_D^{20} = + 234° \pm 5°$ (c = 0.1; methanol containing 0.1% of pure hydrochloric acid).

The infra-red and ultra-violet spectra of this product are identical to those described for the hydrochloride of the antibiotic 13057 R.P. in British Pat. No. 985,598.

We claim:
1. Process for the production of daunorubicin which comprises aerobically cultivating *Streptomyces griseus*, var. *rubidofaciens*, DS 32,041, in an aqueous nutrient medium containing assimilable sources of carbon, nitrogen and inorganic substances, until sufficient amount of the antibiotic is produced and separating daunorubicin formed during the culture.

2. Process according to claim 1 in which the culture is effected under submerged aerobic culture conditions commencing at a pH within the range 6.0 to 7.8 and at a temperature of from 23° to 33° C.

3. Process according to claim 1 in which the pH of the nutrient medium at the beginning of the culture is from 6.5 to 7.5.

4. Process according to claim 1 in which the temperature of the culture is 25° to 30° C.

5. Process according to claim 1 in which the culture medium is aerated at a rate of from 0.3 to 3 liters of air per liter of medium per minute.

6. Process according to claim 1 in which daunorubicin is separated from the culture medium by filtering the medium at a pH between 1.5 and 9, and extracting the daunorubicin from the filtrate using a solvent which is immiscible with water, at a pH between 5.5 and 9.

7. Process according to claim 1 in which daunorubicin is separated from the culture medium by filtering the medium at a pH between 2 and 7 in the presence of an aliphatic alcohol containing from 1 to 3 carbon atoms, extracting the daunorubicin from the filtrate using a solvent which is immiscible with water, at a pH between 5.5 and 9.

8. Process according to claim 1 in which daunorubicin is separated from the culture medium by direct extraction with a water-immiscible solvent, and filtering off the resultant solution containing the antibiotic.

9. Process according to claim 6 in which the water-immiscible solvent used for the extraction of daunorubicin is butanol, methyl isobutyl ketone, ethyl acetate or chloroform.

10. Process according to claim 9 in which daunorubicin is separated from its organic solution by concentrating the solution and precipitating the antibiotic by addition of hexane.

11. Process according to claim 7 in which the water-immiscible solvent used for the extraction of daunorubicin is butanol, methyl isobutyl ketone, ethyl acetate or chloroform.

12. Process according to claim 11 in which daunorubicin is separated from its organic solution by concentrating the solution and precipitating the antibiotic by addition of hexane.

* * * * *